United States Patent [19]

Roy et al.

[11] Patent Number: 5,240,959
[45] Date of Patent: Aug. 31, 1993

[54] ARANOROSINOL-A AND ARANOROSINOL-B PRODUCED BY PSEUDOARACHNIOTUS ROSEUS

[75] Inventors: Kirity Roy; Erra K. S. Vijayakumar; Ravi G. Bhat; Triptikumar Mukhopadhyay; Bimal N. Ganguli, all of Bombay, India

[73] Assignee: Hoechst Aktiengesellschaft, Frankfurt am Main, Fed. Rep. of Germany

[21] Appl. No.: 853,040

[22] Filed: Mar. 18, 1992

[30] Foreign Application Priority Data

Mar. 20, 1991 [EP] European Pat. Off. ...... 91 104 313.1

[51] Int. Cl.$^5$ .................. C07D 311/96; C12P 17/18; C12N 1/00; A61K 39/00
[52] U.S. Cl. .................. 514/462; 549/331; 435/119; 435/822; 424/85.8
[58] Field of Search ............... 435/119, 822; 424/85.8; 549/330, 331, 332, 333, 336, 341, 345; 514/462

[56] References Cited

U.S. PATENT DOCUMENTS

| | | | |
|---|---|---|---|
| 3,991,052 | 11/1976 | Berg et al. | 260/243 R |
| 4,535,183 | 8/1985 | Kneen | 514/568 |
| 5,064,856 | 11/1991 | Garrity et al. | 514/462 |
| 5,112,858 | 5/1992 | Roy et al. | 514/462 |

FOREIGN PATENT DOCUMENTS 0411703 2/1991 European Pat. Off. .

OTHER PUBLICATIONS

H. Fehlhaber et al., "Aranorosin, a Novel Antibiotic from *Pseudoarachniotus roseus*," J. Antibiotics, vol. 41, No. 12, pp. 1785–1794 (1988).

*Primary Examiner*—Douglas W. Robinson
*Assistant Examiner*—Deborah K. Ware
*Attorney, Agent, or Firm*—Finnegan, Henderson, Farabow, Garrett & Dunner

[57] ABSTRACT

Aranorosinol-A and Aranorosinol-B are compounds of the formula

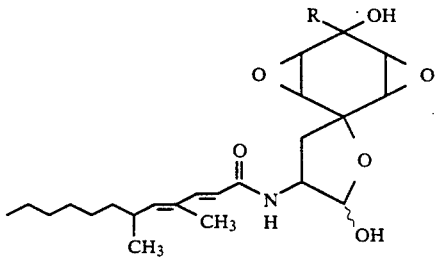

in which R is H (Aranorosinol-A) or $CH_2COCH_3$ (Aranorosinol-B); said compounds have antibacterial and antifungal activity.

2 Claims, 4 Drawing Sheets

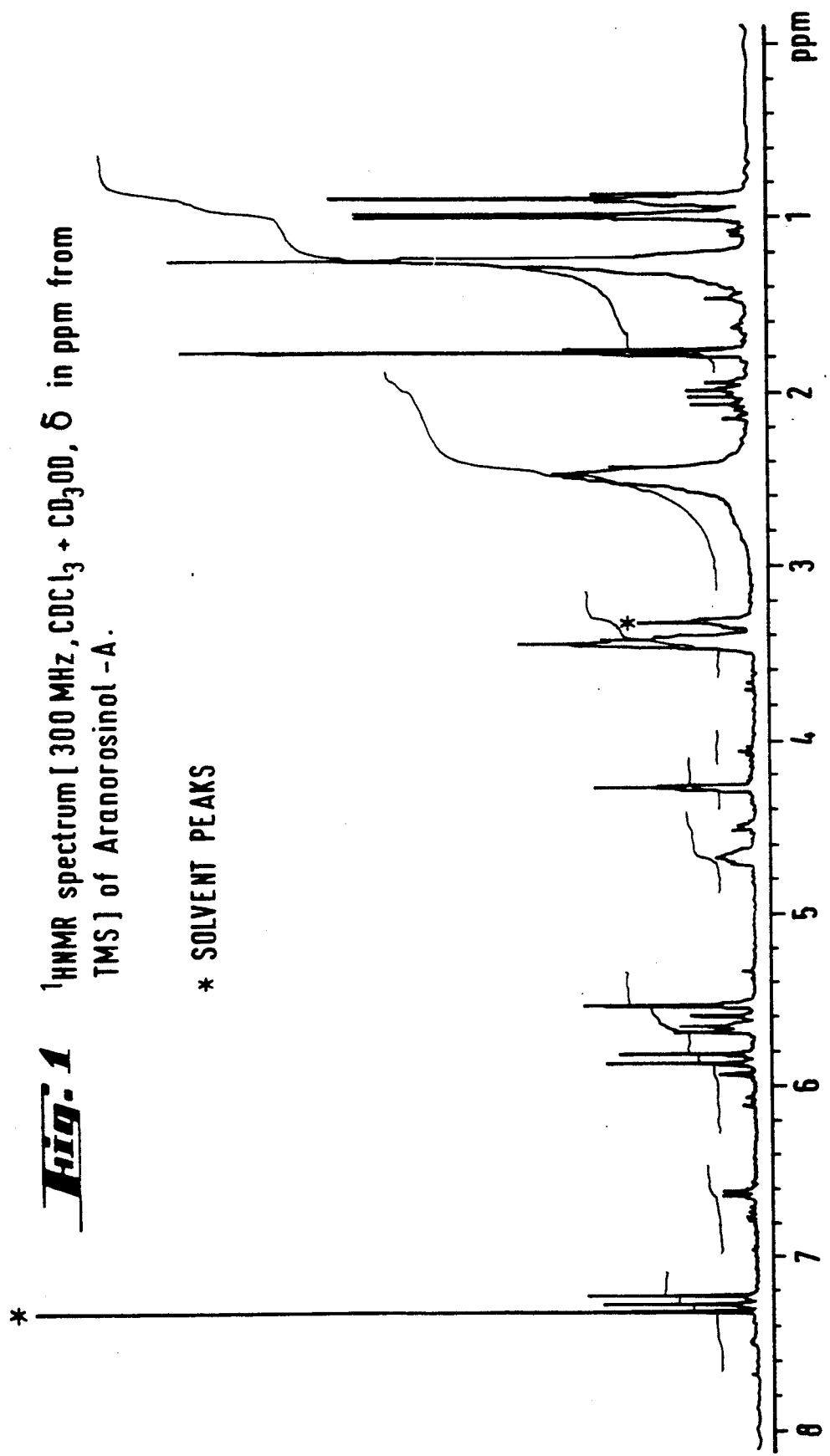

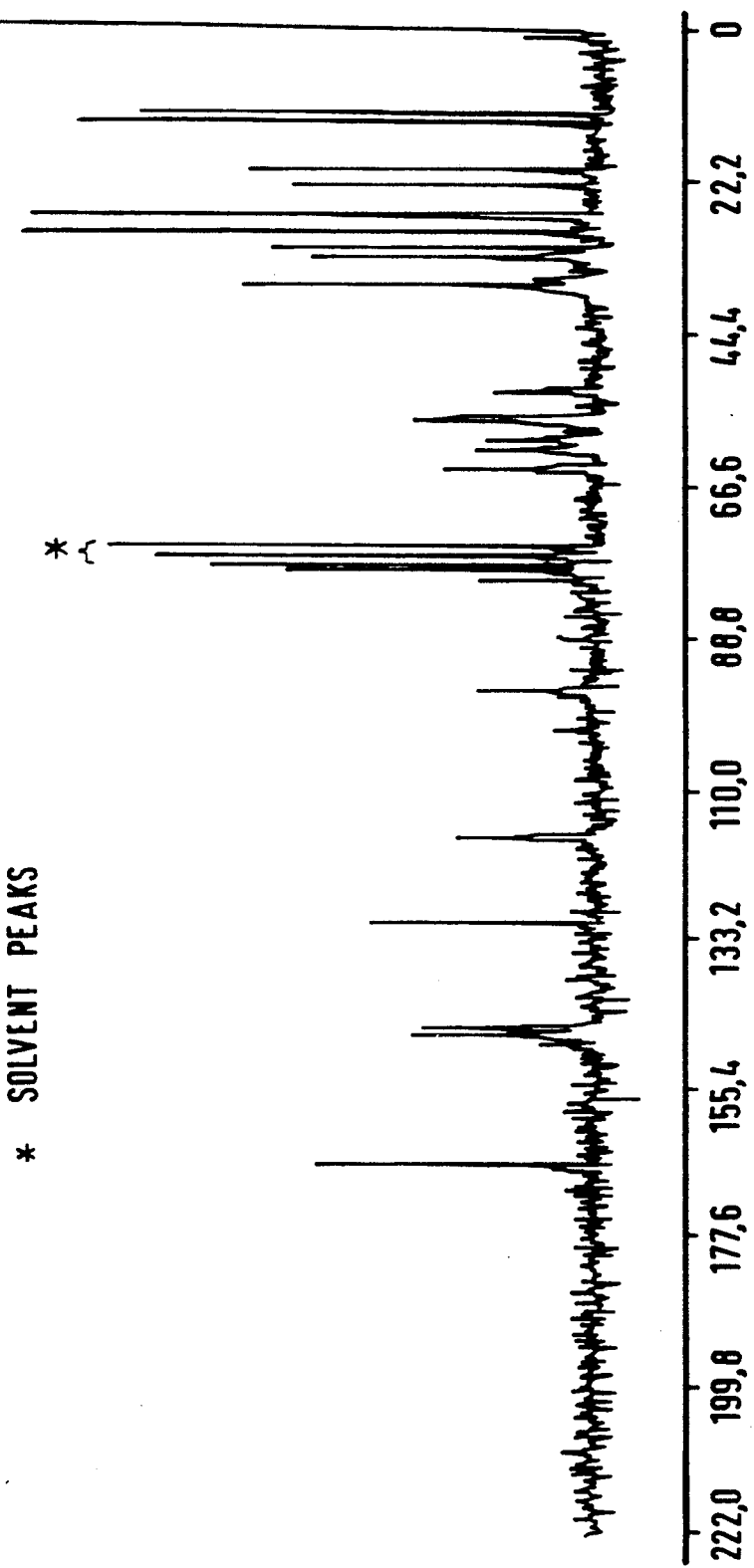

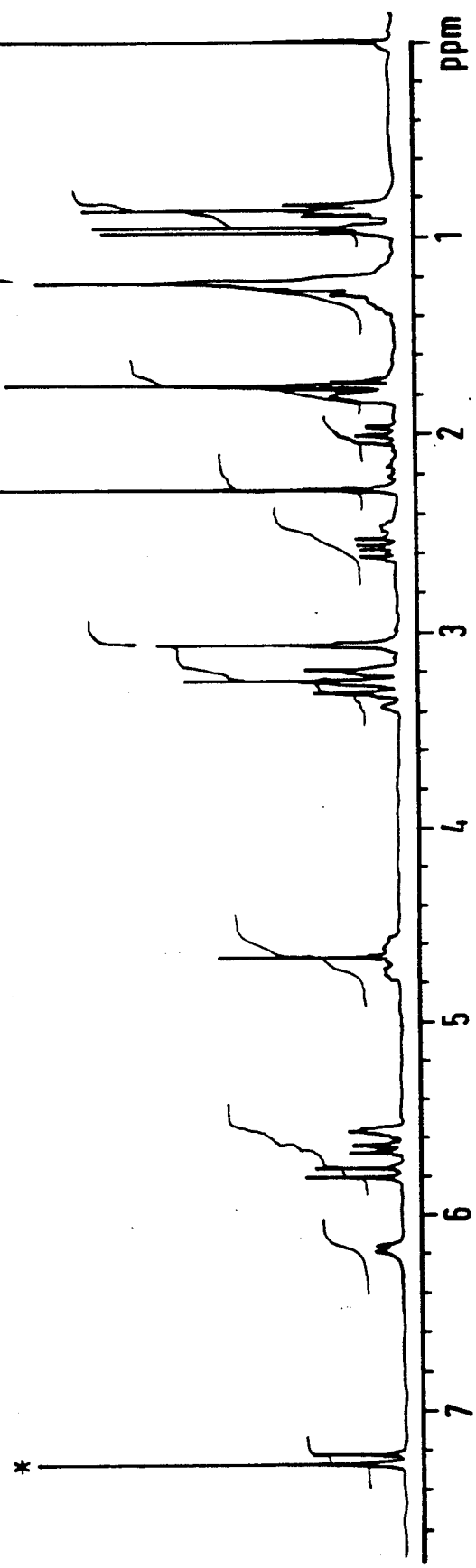
Fig. 3 ¹HNMR spectrum [300 MHz, CDCl₃, δ in ppm from TMS] of Aranorosinol-B.
* SOLVENT PEAK

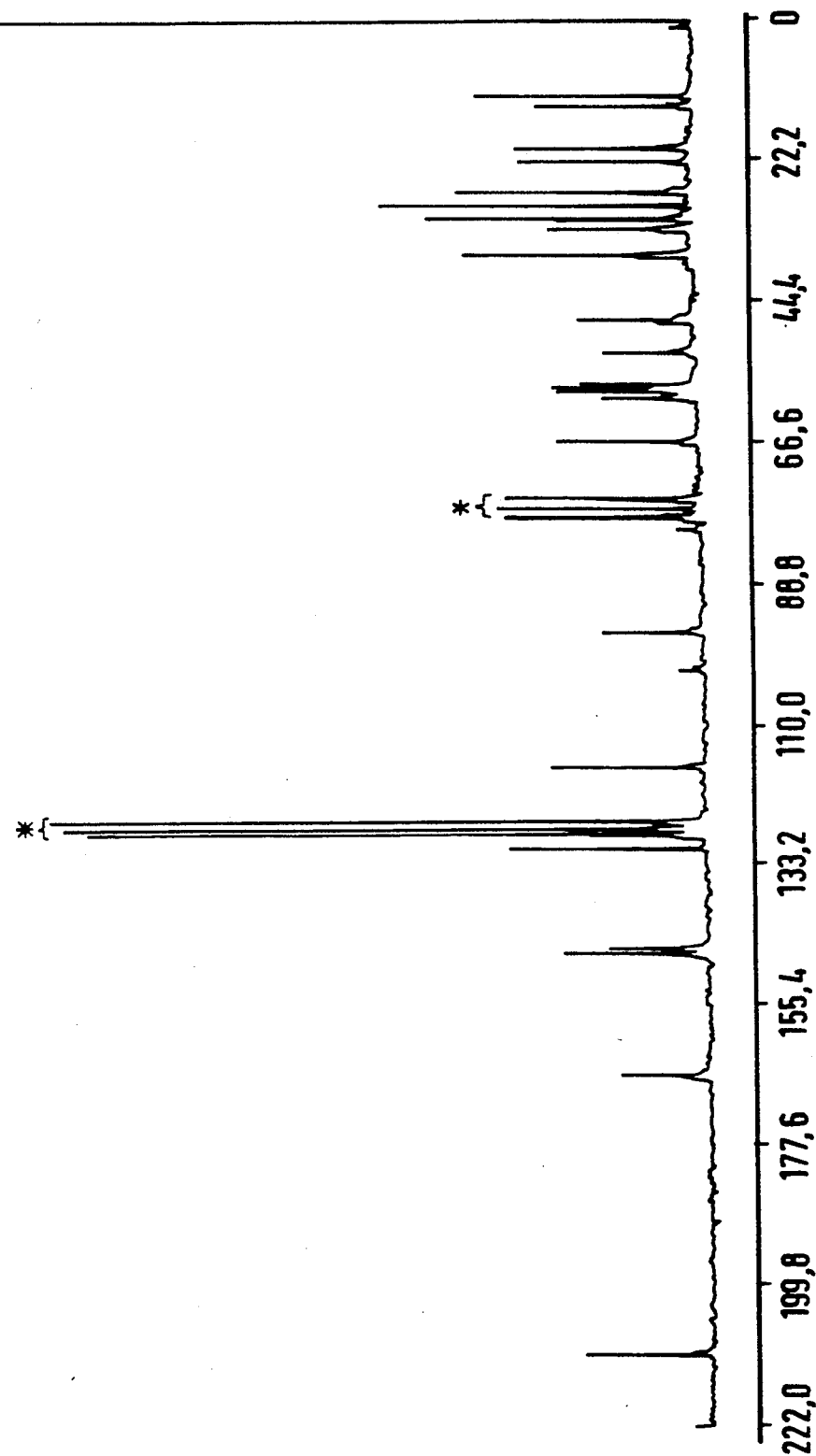
Fig. 4. 13C-NMR spectrum [22,5 MHz, $CDCl_3$ + $C_6D_6$, δ in ppm from TMS] of Aranorosinol-B.
* SOLVENT PEAKS

ARANOROSINOL-A AND ARANOROSINOL-B PRODUCED BY *PSEUDOARACHNIOTUS ROSEUS*

This invention relates to two new antibiotics herein named Aranorosinol-A and Aranorosinol-B a process for their production by fermentation of the microorganism *Pseudoarachniotus roseus* (Culture number Y-30,499) their isolation and use as antibiotics.

Aranorosinol-A and Aranorosinol-B, have the following structures

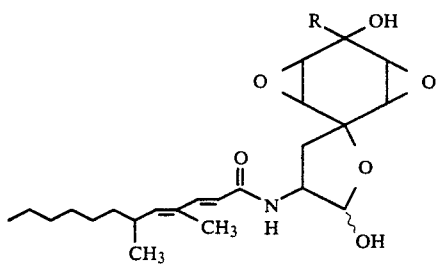

wherein R=H (Aranorosinol-A) or CH$_2$COCH$_3$ (Aranorosinol-B).

According to the present invention there is provided a process for the production of the above-mentioned new antibiotics called Aranorosinol-A and Aranorosinol-B from the microorganism *Pseudoarachniotus roseus* Kuehn Culture No. Y-30,499. Said microorganism has been deposited under the conditions of the Treaty of Budapest on Jun. 23, 1987 (DSM 4151) as outlined in the European Patent application 0341649, in which Aranorosin, a compound of the formula

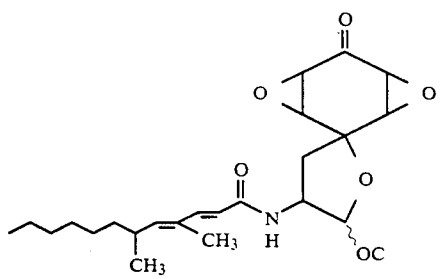

is disclosed. The process comprises cultivation of Y-30,499 by fermentation under aerobic conditions in a nutrient medium containing sources of carbon and nitrogen, nutrient inorganic salts and trace elements, and isolating and purifying the said compounds from the culture broth.

Carbon sources may be glucose, sucrose, starch or dextrin. The preferred carbon source is starch. Sources of nitrogen may be soyabean meal, tryptone, yeast extract, beef extract, malt extract, cornsteep liquor, peptone or inorganic materials such as ammonium salts. The preferred nitrogen source is soyabean meal. Nutrient inorganic salts may be sodium chloride, potassium chloride, hydrogen and dihydrogen phosphate, calcium carbonate. Trace elements may be salts of iron, manganese, copper, zinc, cobalt or of such other heavy metals.

Cultivation of Y-30,499 may be carried out at temperatures varying from 24° C. to 30° C. and a pH between 6.0 and 8.0. Preferably Y-30,499 is cultivated at 26° C. (±1° C.) and pH 6.5.

Fermentation can be carried out in both shake flasks as well as fermenters. "Desmophen" ® (linear polyether derived from propylene oxide) of Bayer AG may be used as an antifoaming agent in the fermenter. The fermentation is preferably stopped between 66 to 90 hrs, when the optimal yield of the compounds of the present invention has been found to have been obtained. The optimum time of harvest is about 72 hrs. The fermentation may, preferably, be submerged fermentation. The progress of the fermentation and formation of Aranorosinol-A and Aranorosinol-B of the present invention can be detected by measuring the bioactivity of the culture broth against *Bacillus subtilis* by the known agar plate diffusion assay method (Assay method of antibiotics, a laboratory manual, 1955 by Grove, D. C. and Randell, W. A., Medical Encyclopaedia Inc., New York).

Aranorosinol-A and Aranorosinol-B of the present invention are isolated from the culture broth and purified by standard laboratory techniques.

Aranorosinol-A and Aranorosinol-B in the culture filtrate are recovered by extraction with a water immiscible solvent such as ethyl acetate, chloroform or butanol. The preferred solvent is ethyl acetate.

The new compounds Aranorosinol-A and Aranorosinol-B of the present invention in the mycelium are preferably recovered by extracting the mycelium, which has been obtained by filtration or centrifugation, with solvents such as ethyl acetate, chloroform, methanol, ethanol, acetone or butanol. The preferred solvent is acetone. After extraction, the solvent can be removed by evaporation under vacuum and the aqueous layer can be diluted with water and reextracted with a solvent such as ethyl acetate.

The solvent extracts from both culture filtrate and mycelium can be combined and evaporated to dryness. From this crude antibiotic mixture Aranorosinol-A, Aranorosinol-B and Aranorosin can be purified by using either normal or reversed phase column chromatography or counter current chromatography or gel filtration chromatography. The techniques may be used repeatedly or a suitable combination of the different techniques may be used for the purification. The preferred method is repeated column chromatography on silica gel.

The following examples are illustrative of the present invention:

EXAMPLE 1

Maintenance of the culture number Y-30,499

Culture Y-30,499 was maintained on Sabouraud's glucose agar medium having the following composition:

| | |
|---|---|
| Glucose | 40 g |
| Peptone | 10 g |
| Na$_2$HPO$_4$ | 1 g |
| Agar | 15 g |
| Distilled water | 1 L |
| pH | 6.5 |

The medium was distributed in test tubes after dissolving the ingredients thoroughly by heating and then sterilized at 121° C. for 20 minutes. The pH prior to autoclaving was 6.5. The test tubes were cooled in a slanting position for preparation of agar slants. The agar slants were inoculated with the spores of culture number Y-30,499 isolated from soil and incubated at 26° C.

(±1° C.) until a good sporulation was observed. The well sporulated cultures were stored in the refrigerator.

EXAMPLE 2

Cultivation of the culture Y-30,499 in shake flasks for the fermentative production of the new antibiotics, Aranorosinol-A and Aranorosinol-B Composition of seed culture medium:

| | |
|---|---|
| Soluble starch | 15 g |
| Soyabean meal | 15 g |
| Glucose | 5 g |
| $CaCO_3$ | 2 g |
| NaCl | 5 g |
| Yeast Extract | 2 g |
| Cornsteep Liquor | 1 g |
| Distilled water | 1 L |

The above seed culture medium was distributed in 100 ml amounts in 500 ml wide mouth Erlenmeyer flasks and sterilized at 121° C. for 20 minutes. pH was adjusted to 6.5 prior to autoclaving. pH after autoclaving was 6.0. The flasks were cooled and then inoculated with few loopfuls of the well-sporulated culture of Example 1 and shaken at 240 rpm for 60 hours at 26° C. (±1° C.) when a good growth was observed. This was used as seed culture for inoculating the production medium.

Composition of the production medium:

| | |
|---|---|
| Soyabean meal | 20 g |
| Glucose | 30 g |
| $CaCO_3$ | 6 g |
| NaCl | 3 g |
| $NH_4Cl$ | 2.5 g |
| $KH_2PO_4$ | 2 g |
| $ZnSO_4 7H_2O$ | 0.22 g |
| $CaCl_2$ | 0.55 g |
| $MnCl_2 4H_2O$ | 0.5 mg |
| $FeSO_4 7H_2O$ | 0.5 mg |
| $CuSO_4 5H_2O$ | 0.16 mg |
| $CoCl_2 6H_2O$ | 0.16 mg |
| Distilled water | 1 L |

The above production medium was distributed in 200 ml amounts in 1 liter Erlenmeyer flasks and sterilized at 121° C. for 20 minutes. The pH of the medium was adjusted to 6.3 prior to autoclaving. After autoclaving the pH was 6.0. The flasks were cooled and then inoculated with the seed culture [1% v/v]. The fermentation was carried out on a rotary shaker at 26° C. (±1° C.) for 72 hours.

After harvesting, the culture fluid was centrifuged and the new antibiotics Aranorosinol-A and Aranorosinol-B were isolated from both the mycelium and the filtrate as described in Example 4.

EXAMPLE 3

Cultivation of the culture Y-30,499 in fermenters for the fermentative production of the new antibiotics Aranorosinol-A and Aranorosinol-B Stage I: Preparation of seed culture
a) In shake flasks:
The seed culture medium, 100 ml, (as mentioned in Example 2) was taken in 500 ml wide mouth Erlenmeyer flasks with presterilisation pH adjusted to 6.5. This was sterilized in our autoclave at 121° C. for 20 minutes, cooled and inoculated with few loopfuls of the slant culture of Example 1. The pH after sterilization was 6.0. The flasks were incubated at 26° C. (±1° C.) for 72 hours at 240 r.p.m. on a rotary shaker.

b) In aspirator bottles:
One liter of the seed culture medium (as mentioned in Example 2) was taken in a 5 liter aspirator bottle. This was sterilized in an autoclave at 121° C. for 30 minutes, cooled and inoculated with a few loopfuls from the slant culture of Example 1. The pH of the medium was 6.5 before sterilization and 6.0 after sterilization. The bottles were mounted on a rotary shaker and incubated for 72 hours at 26° C. (±1° C.) at 240 r.p.m.

Stage II: Fermentation
a) Small Scale:
Ten liters of the production medium (as mentioned in Example 2) with 0.04% Desmophen in a 15 liter stainless steel fermenter were autoclaved at 121°–122° C. for 36 minutes. The pH before sterilization was 6.5 and after sterilization was 6.0.

Twenty liters of the production medium (as mentioned in Example 2) with 0.04% Desmophen were taken in a 30 liter, stainless steel fermenter and were sterilized in situ for 32 minutes at 122° C. at 1.2 kg/cm² steam pressure. The presterilization pH was adjusted to 6.5. pH after sterilization was 6.0. After cooling, they were inoculated with 1–3% (v/v) of seed culture under aseptic conditions and run at 26° C. (±1° C.), with an agitation of 120–180 r.p.m. depending upon growth and foaming and an aeration of 6–10 l.p.m.

b) Large Scale:
One hundred liter of the production medium (as mentioned in Example 2) were taken in a 150 liter fermenter with presterilization. pH adjusted to 6.5 and with 0.04% Desmophen. The medium was sterilized in situ at 121°–122° C. for 32 minutes at 1.2 kg/cm² steam pressure. pH after sterilization was 6.0. After cooling to 26° C., it was inoculated with 1% of seed culture from the aspirator bottle under aseptic conditions and was run at a temperature of 26° C. (±1° C.) with an agitation of 100 r.p.m. and aeration of 60 l.p.m.

The fermenters were harvested at 72 hours and the production of Aranorosinol-A and Aranorosinol-B was determined by the activity tested against *Bacillus subtilis*.

The harvested broth was centrifuged and processed further as described in Example 4.

EXAMPLE 4

Isolation, purification and identification of Aranorosinol-A and Aranorosinol-B

Approximately 300 liters of the fermentation broth were centrifuged to separate the mycelium and the culture filtrate.

The culture filtrate (270 liters) which was at pH 6.2 was extracted twice each with 90 liters of ethyl acetate. The combined extracts were freed from solvent under reduced pressure at 35° C.

The mycelial cake (24.5 kg) was extracted twice with acetone-each time with 50 liters of the solvent. Most of the solvent was removed from the combined extract under reduced pressure at 35° C. and the residual aqueous phase was diluted with water and extracted twice with 5 liters of the ethyl acetate. The ethyl acetate extracts were concentrated under reduced pressure at 35° C. and combined with the concentrate from the culture filtrate extract.

The reddish brown crude antibiotic mixture (125 g) was chromatographed on silica gel (1.65 kg, 230–400 mesh) under pressure (Flow rate: 50 ml/min.). The column was eluted with chloroform-methanol mixtures with increasing amounts of methanol until a concentration of 10% methanol in chloroform was reached.

A mixture of Aranorosinol-B and Aranorosin eluted between 2-3% methanol in chloroform, while Aranorosinol-A eluted between 5-10% methanol in chloroform.

The semipure Aranorosinol-A (25 g) was rechromatographed on silica gel (400 g, 230-400 mesh) under pressure (flow rate: 40 ml/min.) using 5% methanol in chloroform as eluant. Pure Aranorosinol-A (7.5 g) was isolated as a white solid. This material may be dissolved in ethyl acetate or chloroform and precipitated with n-hexane to remove traces of pigments.

The mixture of Aranorosinol-B and Aranorosin (24.5 g) was separated on a silica gel (1.1 kg, 230-400 mesh) column which was eluted with petroleum ether-ethyl acetate mixtures with increasing concentration of ethyl acetate in petroleum ether. Pure Aranorosin (3.8 gm) eluted in 1:1 petroleum ether-ethyl acetate while Aranorosinol-B (240 mg) in 1:3 petroleum ether-ethyl acetate. Aranorosinol-B thus isolated may be dissolved in ethyl acetate or chloroform and precipitated with n-hexane to remove traces of pigments.

Aranorosinol-A and Aranorosinol-B were analysed by chemical analysis and spectroscopic methods. They exhibit the following characteristics.

| | Aranorosinol-A | Aranorosinol-B |
|---|---|---|
| 1. Appearance | White solid | White solid |
| 2. Molecular formula | $C_{23}H_{35}NO_6$ | $C_{26}H_{39}NO_7$ |
| 3. Molecular weight | 421 | 477 |
| 4. Melting point | 133-135° C. | 84-85° C. |
| 5. $[\alpha]_D^{20}$ | −25.06° (C = 7.82 mg/ml in methanol) | −9.3° (C = 4.08 mg/ml in $CHCl_3$) |
| 6. Rf (Thin layer chromatography on precoated silica gel plates) | 0.38 (85:15 chloroform-methanol) 0.13 (Ethylacetate) | 0.55 (85:15 chloroform-methanol) 0.25 (Ethylacetate) |
| 7. Elemental analysis | C, 62.45; H, 8.32; N, 3.45 | C, 64.91; H, 8,89 N, 3.27 |
| 8. Solubility | Insoluble in n-hexane water, soluble in dichloromethane, chloroform, acetone methanol, diethyl ether, ethyl acetate and dimethyl sulfoxide | Insoluble in n-hexane water, soluble in dichloromethane, chloroform, acetone methanol, diethyl ether, ethyl acetate and dimethyl sulfoxide |
| 9. UV (methanol) | $\lambda max^{266\ nm}$ | $\lambda max^{265\ nm}$ |
| 10. $^1H$—NMR | See FIG. 1 of the accompanying drawings 300 MHz, $CDCl_3 + CD_3OD$, $\delta$ in ppm from TMS) *represents | See FIG. 3 of the accompanying drawings (300 MHz, $CDCl_3$, $\delta$ in ppm from TMS) *represents |
| 11. $^{13}C$—NMR | solvent peaks See FIG. 2 of the accompanying drawings (22.5 MHz, $CDCl_3$, $\delta$ in ppm from TMS) *represents solvent peaks | solvent peaks See FIG. 4 of the accompanying drawings (22.5 MHz, $CDCl_3$ + $C_6D_6$, $\delta$ in ppm from TMS) *represents solvent peaks |

The minimum inhibitory concentrations required to inhibit different bacteria and fungal strains by Aranorosinol-A and Aranorosinol-B are given in Table I

TABLE I

| | Minimum inhibitory concentration in micrograms per milliliter | |
|---|---|---|
| Test Organisms | Aranorosinol-A | Aranorosinol-B |
| Staphylococcus aureus 209 P | 15.6 | 31.25 |
| Staphylococcus aureus 20240 | 31.25 | 15.62 |
| Bacillus subtilis | 3.9 | 15.62 |
| Streptococcus faecalis | 31.25 | 125.00 |
| E. coli Ess 2231 | 62.5 | >250.00 |
| E. coli 9632 | >250.00 | >250.00 |
| Proteus vulgaris | >250.00 | >250.00 |
| Salmonella typhimurium | >250.00 | >250.00 |
| Klebsiella pneumoniae | >250.00 | >250.00 |
| Pseudomonas aeruginosa | >250.00 | >250.00 |
| Candida albicans | 62.5 | 250.00 |
| Saccharomyces cerevisiae | 31.25 | 250.00 |
| Aspergillus niger | >250.00 | >250.00 |
| Trichophyton mentagrophytes | 62.5 | >250.00 |
| Microsporum | >250.00 | >250.00 |

Aranorosinol-A is thus active against Gram-positive, Gram-negative bacteria and against yeast and filamentous fungi, while Aranorosinol-B is active against Gram-positive bacteria only.

We claim:

1. A compound having the formula

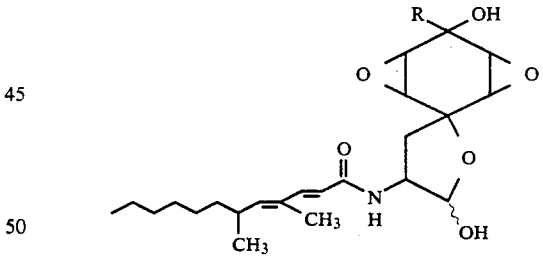

wherein R is H or $CH_2COCH_3$.

2. A pharmaceutical composition comprising an antibacterial or antifungal effective amount of at least one compound of claim 1 in combination with a pharmaceutically acceptable carrier.

* * * * *